US012582489B2

(12) United States Patent
Hares et al.

(10) Patent No.: US 12,582,489 B2
(45) Date of Patent: Mar. 24, 2026

(54) MOUNTING AN ENDOSCOPE TO A SURGICAL ROBOT

(71) Applicant: CMR SURGICAL LIMITED, Cambridge (GB)

(72) Inventors: Luke David Ronald Hares, Cambridge (GB); James Oliver Grant, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 0 days.

(21) Appl. No.: 18/064,323

(22) Filed: Dec. 12, 2022

(65) Prior Publication Data

US 2023/0105679 A1     Apr. 6, 2023

Related U.S. Application Data

(62) Division of application No. 16/483,797, filed as application No. PCT/GB2018/050336 on Feb. 6, 2018, now Pat. No. 11,547,502.

(30) Foreign Application Priority Data

Feb. 7, 2017     (GB) ..................................... 1702006

(51) Int. Cl.
*A61B 1/00*          (2006.01)
*A61B 17/00*          (2006.01)
(Continued)

(52) U.S. Cl.
CPC .......... *A61B 34/30* (2016.02); *A61B 1/00128* (2013.01); *A61B 1/00142* (2013.01);
(Continued)

(58) Field of Classification Search
CPC . A61B 34/30; A61B 1/00128; A61B 1/00142; A61B 1/00112; A61B 46/10;
(Continued)

(56) References Cited

U.S. PATENT DOCUMENTS

| 6,063,095 | A | 5/2000 | Wang et al. |
| 6,451,027 | B1 | 9/2002 | Cooper et al. |

(Continued)

FOREIGN PATENT DOCUMENTS

| CN | 101340853 A | 1/2009 |
| CN | 104414737 A | 3/2015 |

(Continued)

OTHER PUBLICATIONS

Chinese Notice of the Granting of a Patent Right for an Invention from corresponding Chinese Application No. 201880010416.8 dated Jan. 28, 2023.

(Continued)

*Primary Examiner* — Anh Tuan T Nguyen
*Assistant Examiner* — Rynae E Boler
(74) *Attorney, Agent, or Firm* — Lando & Anastasi, LLP

(57)     ABSTRACT

A surgical endoscope for manipulation by a surgical robot arm. The surgical endoscope comprises a shaft having a distal end for insertion into a patient and a proximal end. An endoscope interface is attached to the proximal end of the shaft. The endoscope interface is configured to engage a robot arm interface of the surgical robot arm. The endoscope interface comprises an endoscope wedge mechanism moveable between an unlocked position and a locked position. The endoscope wedge mechanism comprises endoscope wedge elements which are displaceable such that collective displacement of the endoscope wedge elements actuates the endoscope wedge mechanism between the unlocked position and the locked position.

16 Claims, 10 Drawing Sheets

(51) Int. Cl.
  *A61B 34/30* (2016.01)
  *A61B 46/10* (2016.01)

(52) U.S. Cl.
  CPC .... *A61B 46/10* (2016.02); *A61B 2017/00486* (2013.01); *A61B 2034/301* (2016.02); *A61B 2034/305* (2016.02)

(58) Field of Classification Search
  CPC ........... A61B 2017/00486; A61B 2017/00477; A61B 2034/301; A61B 2034/305
  See application file for complete search history.

(56) References Cited

U.S. PATENT DOCUMENTS

| | | | |
|---|---|---|---|
| 2002/0120363 A1 | 8/2002 | Salisbury et al. | |
| 2003/0125716 A1 | 7/2003 | Wang et al. | |
| 2006/0161136 A1 | 7/2006 | Anderson et al. | |
| 2007/0119274 A1 | 5/2007 | Devengenzo et al. | |
| 2007/0142970 A1 | 6/2007 | Burbank et al. | |
| 2007/0270640 A1 | 11/2007 | Dimitriou et al. | |
| 2009/0024142 A1* | 1/2009 | Ruiz Morales ........ | A61B 34/37 606/130 |
| 2010/0274078 A1 | 10/2010 | Kim et al. | |
| 2012/0010628 A1 | 1/2012 | Cooper et al. | |
| 2012/0088963 A1 | 4/2012 | Yasunaga et al. | |
| 2012/0165828 A1 | 6/2012 | Duque et al. | |
| 2013/0338679 A1 | 12/2013 | Rosielle et al. | |
| 2014/0114126 A1 | 4/2014 | Dresher | |
| 2015/0257841 A1 | 9/2015 | Dachs, II | |
| 2015/0374445 A1 | 12/2015 | Gombert et al. | |
| 2016/0058513 A1* | 3/2016 | Giorgi .................... | A61B 46/10 606/130 |
| 2016/0089008 A1 | 3/2016 | Simmons | |
| 2016/0151115 A1 | 6/2016 | Karguth et al. | |
| 2016/0157941 A1 | 6/2016 | Anvari et al. | |
| 2016/0310222 A1 | 10/2016 | Kottenstette | |
| 2016/0361123 A1 | 12/2016 | Hares et al. | |
| 2018/0168752 A1 | 6/2018 | Scheib et al. | |

FOREIGN PATENT DOCUMENTS

| | | | | | |
|---|---|---|---|---|---|
| CN | 104936502 A | 9/2015 | | | |
| CN | 105578945 A | 5/2016 | | | |
| EP | 3072471 A1 | 9/2016 | | | |
| GB | 2523831 A | * | 9/2015 | ............. | A61B 34/00 |
| IN | 104688281 A | 6/2015 | | | |
| JP | H5-192886 A | 8/1993 | | | |
| JP | 2001299680 A | 10/2001 | | | |
| JP | 2009525098 A | 7/2009 | | | |
| JP | 2012005557 A | 1/2012 | | | |
| JP | 2016120277 A | 7/2016 | | | |
| WO | 199516396 A1 | 6/1995 | | | |
| WO | 2010111090 A1 | 9/2010 | | | |
| WO | 2011143016 A1 | 11/2011 | | | |
| WO | 2014126757 A2 | 8/2014 | | | |
| WO | 2015010189 A1 | 1/2015 | | | |
| WO | 2016097861 A1 | 6/2016 | | | |
| WO | 2016176170 A1 | 11/2016 | | | |
| WO | 2016178028 A1 | 11/2016 | | | |

OTHER PUBLICATIONS

Japanese Decision to Grant a Patent from corresponding Japanese Patent Application No. 2022-200376 dated Feb. 2, 2024.

Communication under Rule 71(3) Intention to Grant from corresponding European Application No. 18705457.2 dated Apr. 14, 2021.

European Examination Report from corresponding European Application No. 18705457.2 dated Sep. 24, 2020.

Extended European Search Report from corresponding European Application No. 22177742.8 dated Sep. 8, 2022.

Japanese Decision of Refusal from corresponding Japanese Patent Application No. 2019-542534 dated Aug. 18, 2022.

Japanese Notification of Reasons for Refusal from corresponding Japanese Patent Application No. 2019-542534 dated Dec. 22, 2021.

Notification of Transmittal of the International Search Report and the Written Opinion of the International Searching Authority from corresponding PCT/GB2018/050336 dated Sep. 18, 2018.

United Kingdom Combined Search and Examination Report from corresponding United Kingdom Application No. GB2200128.3 dated Jan. 25, 2022.

United Kingdom Examination Report from corresponding United Kingdom Application No. GB2200130.9 dated Jan. 25, 2022.

United Kingdom Search Report from corresponding United Kingdom Application No. GB1702006.6 dated Jun. 12, 2017.

Extended European Search Report from corresponding European Application No. 24170351.1 dated Jul. 15, 2024.

Indian Examination Report from corresponding Indian Application No. 202118041304 dated Jan. 14, 2025.

* cited by examiner

MOUNTING AN ENDOSCOPE TO A SURGICAL ROBOT

CROSS-REFERENCE TO RELATED APPLICATION

This application is a divisional of U.S. patent application Ser. No. 16/483,797, filed on Aug. 6, 2019, which is a U.S. National Phase application under 35 U.S.C. § 371 of International Application No. PCT/GB2018/050336 [Expired], filed Feb. 6, 2018, which claims priority to United Kingdom Application No. 1702006.6, filed Feb. 7, 2017. Each application referenced above is hereby incorporated by reference herein in its entirety for all purposes.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

A typical laparoscopic operation may require several surgical robots, each one carrying an instrument or other implement which is used concurrently with the others at the surgical site. For example, a pair of pincers, a scalpel and an endoscope may all be concurrently manipulated at the surgical site, each of which is attached to a different surgical robot.

Each surgical robot is located around the patient in such a position that its instrument/implement can reach the surgical site via its port and perform the required manipulations at the surgical site. The available space around the patient is limited and is also required by the operating room staff for access to the patient. Ideally, the robot arms are spaced sufficiently far apart that each robot arm can have any joint configuration and not clash with an adjacent robot arm. This spacing can be set by determining the working space of each robot arm to be the total swept volume of the robot arm in all its configurations. If the end of the instrument/implement which interfaces the distal end of the robot arm extends beyond the profile of the distal end of the robot arm, the swept volume of that extension is determined and added to the swept volume of the robot arm to determine the working space of the robot arm. To ensure collisions are avoided, no other apparatus is allowed to encroach into this working space. An alternative approach is to allow one robot arm to be within the working space of another robot arm, but to limit the configurations that one or both of the robot arms can adopt so as to avoid collisions between the two. A complex control system which implements a collision avoidance mechanism is used to accomplish this.

If the end of the instrument/implement which interfaces the distal end of the robot arm is bulky, this also limits the positions at which the port may be located so as to enable access of the instrument/implement to the surgical site of the patient.

Endoscopes are particularly bulky implements due to the optical equipment they house. The end of the endoscope which interfaces the robot arm is typically larger than the equivalent interface on an instrument, and also typically larger than the end of the robot arm to which it attaches.

SUMMARY OF THE INVENTION

According to an aspect of the invention, there is provided a surgical endoscope for manipulation by a surgical robot arm, the surgical endoscope comprising: a shaft having a distal end for insertion into a patient and a proximal end; an endoscope interface attached to the proximal end of the shaft, the endoscope interface configured to engage a robot arm interface of the surgical robot arm, the endoscope interface comprising: an endoscope wedge mechanism moveable between an unlocked position and a locked position, the endoscope wedge mechanism comprising: endoscope wedge elements which are displaceable such that collective displacement of the endoscope wedge elements actuates the endoscope wedge mechanism between the unlocked position and the locked position.

The endoscope interface may be received in the robot arm interface such that the endoscope wedge elements are retained by complementary robot arm wedge elements when the endoscope interface and robot arm interface are engaged.

The endoscope interface may primarily extend parallel to the longitudinal axis of the surgical endoscope and transverse to the longitudinal axis of the surgical endoscope.

Each endoscope wedge element may be displaceable transverse to the longitudinal axis of the surgical endoscope.

Each endoscope wedge element may be biased towards its configuration in the locked position of the endoscope wedge mechanism.

The endoscope wedge elements may be spring-biased towards their configuration in the locked position of the endoscope wedge mechanism.

The surgical endoscope may comprise two endoscope wedge elements configured to be separated by a greater distance in the locked position of the endoscope wedge mechanism than in the unlocked position of the endoscope wedge mechanism.

The endoscope wedge mechanism may further comprise a lock configured to constrain the endoscope wedge elements in a spaced apart configuration in the locked position of the endoscope wedge mechanism, and to not constrain the endoscope wedge elements in the unlocked position of the endoscope wedge mechanism.

The lock may be biased towards its configuration in the locked position of the endoscope wedge mechanism.

The lock may be spring-biased towards its configuration in the locked position of the endoscope wedge mechanism.

An endoscope wedge element may comprise a mating wedge and a projection, the mating wedge configured to mate with a robot arm wedge element of the robot arm interface, the mating wedge further configured to be spaced apart from a mating wedge of the other endoscope wedge element by the lock.

The projection may be configured to, as the endoscope wedge mechanism is actuated from the locked position to the unlocked position, engage the lock so as to move the lock from between the mating wedges thereby permitting the mating wedges to be brought together in the unlocked position.

The projection may be configured to, as the endoscope wedge mechanism is actuated from the locked position to the unlocked position, apply a force to the lock which opposes the direction in which the lock is biased.

The projection may be biased towards its configuration in the locked position of the endoscope wedge mechanism.

The projection may be spring-biased towards its configuration in the locked position of the endoscope wedge mechanism.

The mating wedge and the projection may both be displaceable in the same direction.

The projection may be displaceable relative to the mating wedge.

The projection may be subject to a projection bias force and the mating wedge may be subject to a mating wedge bias force, the projection bias force and mating wedge bias force being in the same bias direction, the mating wedge bias force being greater than the projection bias force, wherein the projection and mating wedge are both configured to be actuated by the same external force applied in an opposing direction to the bias direction.

The endoscope interface may comprise an endoscope assembly and an endoscope drape, the endoscope drape being detachable from the endoscope assembly.

The mating wedge may comprise an endoscope drape wedge element and an endoscope assembly wedge element, the endoscope drape wedge element being detachable from the endoscope assembly wedge element, the endoscope drape wedge element configured to engage directly with the robot arm interface.

According to a second aspect of the invention, there is provided a surgical robot for manipulating a surgical endoscope, the surgical robot comprising: a robot base connected to a distal robot arm link via a series of intermediate articulated robot arm links; a robot arm interface attached to the distal robot arm link, the robot arm interface configured to receive and engage an endoscope interface of the surgical endoscope, the robot arm interface comprising: robot arm interface elements for engaging endoscope interface elements of the endoscope interface, all the robot arm interface elements being static in the robot arm interface, wherein the robot arm interface is shaped so as to only receive and engage the endoscope interface when the endoscope interface and robot arm interface are brought into engagement in a direction perpendicular to the longitudinal axis of the distal robot arm link.

The robot arm interface may primarily extend parallel to the longitudinal axis of the distal robot arm link and transverse to the longitudinal axis of the distal robot arm link.

The robot arm interface may comprise a rim transverse to the longitudinal axis of the distal robot arm link, the rim acting to constrain the robot arm interface to only being able to receive and engage the endoscope interface when the endoscope interface is brought into engagement with the robot arm interface in a direction perpendicular to the longitudinal axis of the distal robot arm link.

The robot arm interface elements may comprise robot arm wedge elements for retaining complementary endoscope wedge elements when the endoscope interface and robot arm interface are engaged.

The robot arm wedge elements may be angled in the direction in which the endoscope interface is brought into engagement with the robot arm interface, such that when the endoscope interface and robot arm interface are engaged, the robot arm wedge elements constrain the endoscope wedge elements in the direction in which the endoscope interface is brought into engagement with the robot arm interface.

The surgical robot may comprise two robot arm wedge elements separated so as to be capable of retaining the endoscope wedge elements between them, wherein the separation of the robot arm wedge elements varies over the robot arm interface.

The robot arm interface may comprise a robot arm assembly and a robot arm drape, the robot arm drape being detachable from the robot arm assembly.

The robot arm drape may comprise the robot arm wedge elements.

According to a third aspect of the invention, there is provided a surgical robot for manipulating a surgical endoscope, the surgical robot comprising: a robot base connected to a distal robot arm link via a series of intermediate articulated robot arm links; a robot arm interface attached to the distal robot arm link; and a surgical endoscope comprising: a shaft having a distal end for insertion into a patient and a proximal end; an endoscope interface attached to the proximal end of the shaft; wherein the robot arm interface is configured to receive and engage the endoscope interface such that the longitudinal axis of the distal robot arm link is aligned with the longitudinal axis of the surgical endoscope.

The distal robot arm link may be attached to a second robot arm link by a roll joint, the longitudinal axis of the surgical endoscope being aligned with the roll axis of the roll joint.

The distal robot arm link may be attached to the second robot arm link by a compound joint, the compound joint permitting the distal robot arm link to rotate about a roll axis, a pitch axis and a yaw axis relative to the second robot arm link, the longitudinal axis of the surgical endoscope intersecting the pitch axis and the yaw axis.

The robot arm interface may be shaped so as to only receive and engage the endoscope interface when the endoscope interface and robot arm interface are brought into engagement in a direction perpendicular to the longitudinal axis of the distal robot arm link and perpendicular to the longitudinal axis of the surgical endoscope.

The surgical endoscope may be operable when detached from the distal robot arm link.

According to a fourth aspect of the invention, there is provided a replica endoscope interface for mating with a robot arm interface of a surgical robot in a process of characterising the environment of the surgical robot, the replica endoscope interface comprising: an endoscope wedge mechanism moveable between an unlocked position and a locked position, the endoscope wedge mechanism comprising: endoscope wedge elements which are displaceable such that collective displacement of the endoscope wedge elements actuates the endoscope wedge mechanism between the unlocked position and the locked position.

BRIEF DESCRIPTION OF THE FIGURES

The present invention will now be described by way of example with reference to the accompanying drawings. In the drawings.

DETAILED DESCRIPTION

Figure 2:
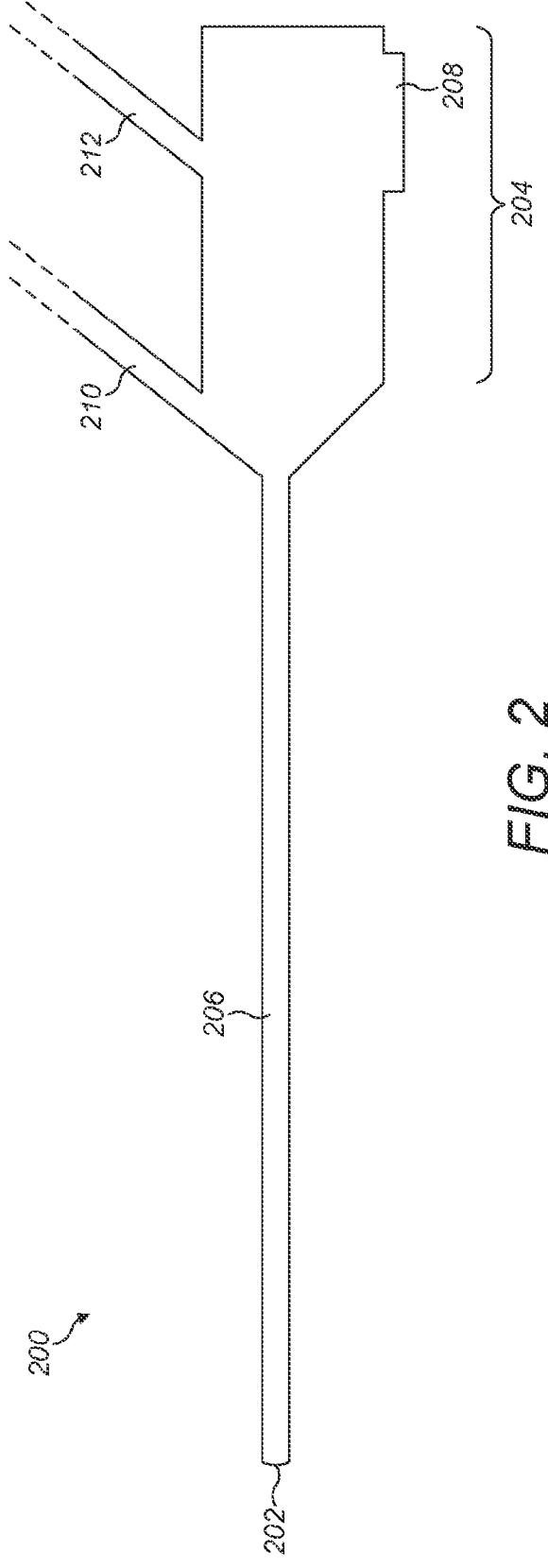
FIG. 2 illustrates a surgical endoscope.

FIG. 2 illustrates an endoscope which is attachable to the end of a robot arm for use in minimally invasive surgery. The endoscope 200 has a distal end 202 for insertion into the surgical site of the patient, and a proximal end 204. The distal end is connected to the proximal end by an elongate shaft 206. The proximal end 204 comprises an interface 208 for engaging the end of the robot arm.

The endoscope has a power source and a light source for illuminating the surgical site. The endoscope also has a data line for extracting the image data from the surgical site. These may all be attached to the proximal end of the endoscope independently and externally of the robot arm, as shown in FIG. 2. In FIG. 2, power is applied through stem 212, image data is extracted through stem 212, and light is applied through light stem 210. In an alternative implementation, any one or more of the light input, power input and data output may be applied/extracted to the endoscope through the robot arm.

Figure 1:
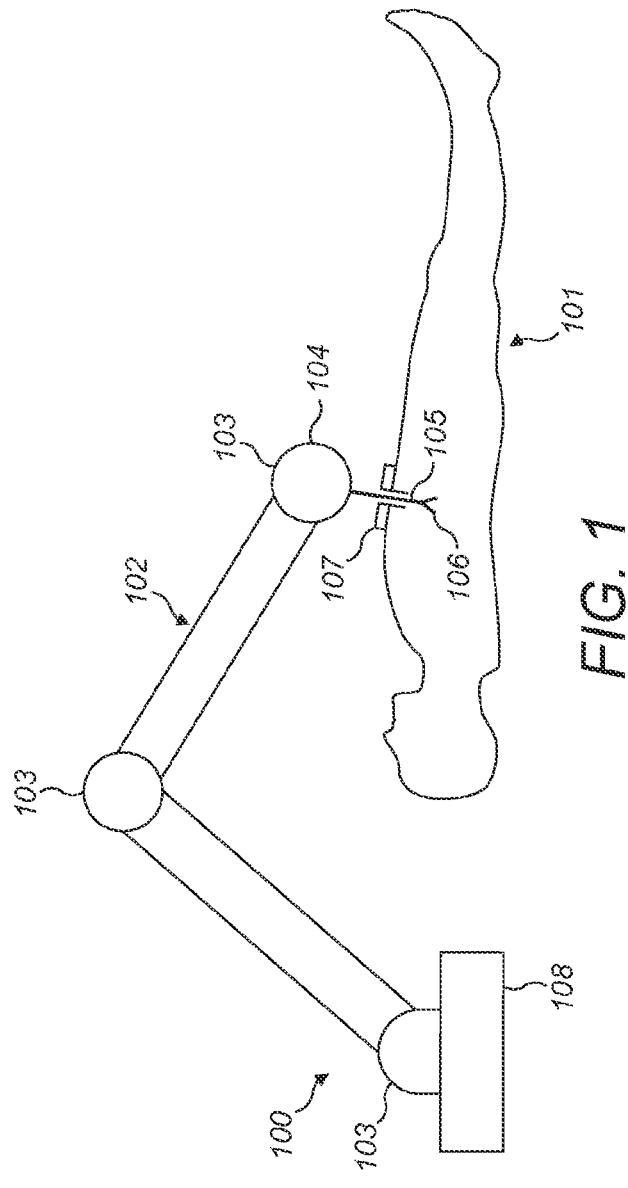
FIG. 1 illustrates a surgical robot performing a surgical procedure.

The endoscope mounts to the end of the robot arm. The robot arm has the form shown in FIG. 1. In other words, the robot arm extends between a base and an interface by which it attaches to the endoscope. The robot arm comprises a series of rigid links interspersed by joints. Those joints enable articulation of the robot arm.

Figure 3A:
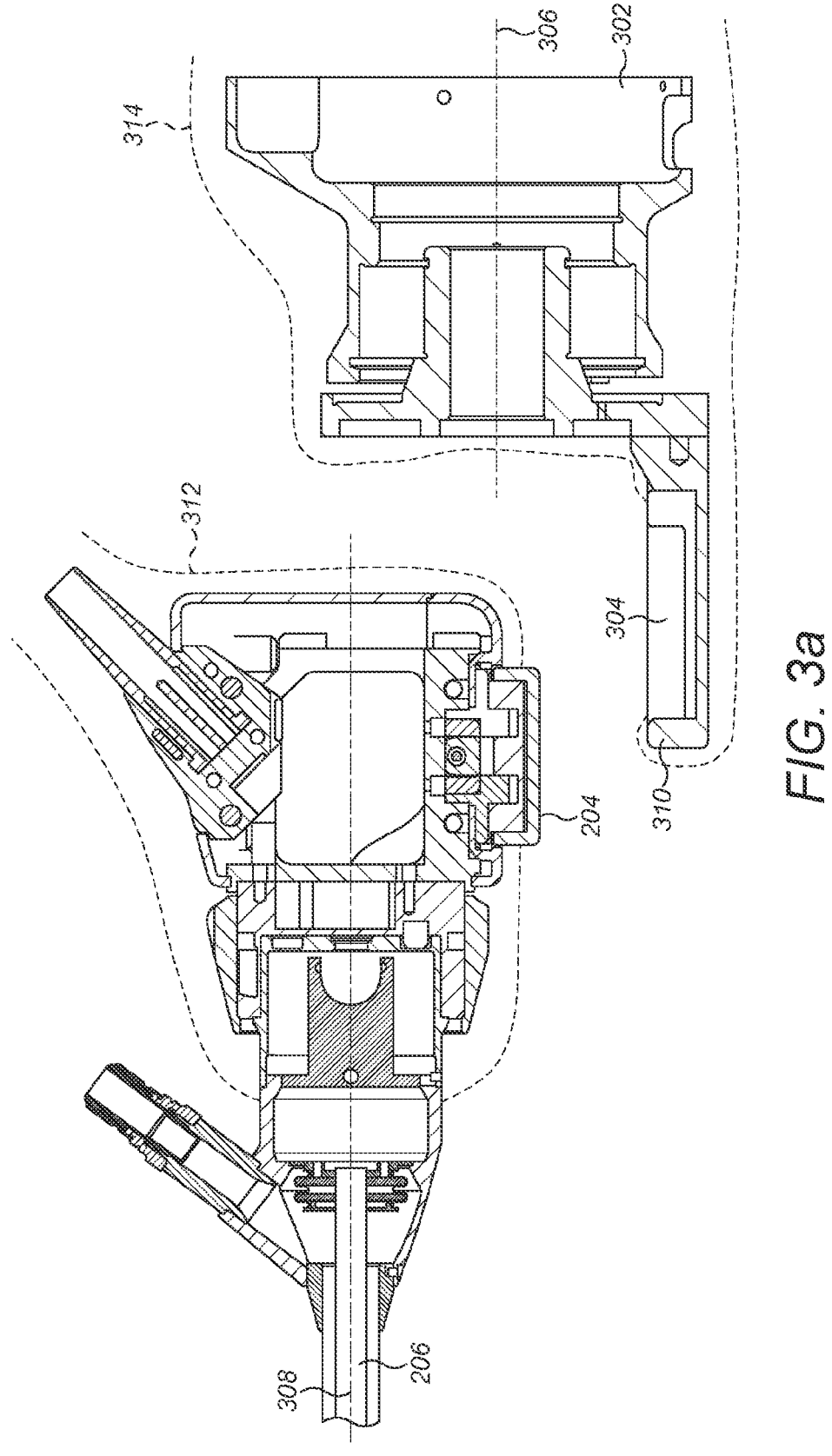
FIGS. 3a and 3b illustrate an endoscope being brought into engagement and engaged with a robot arm.
Figure 3B:
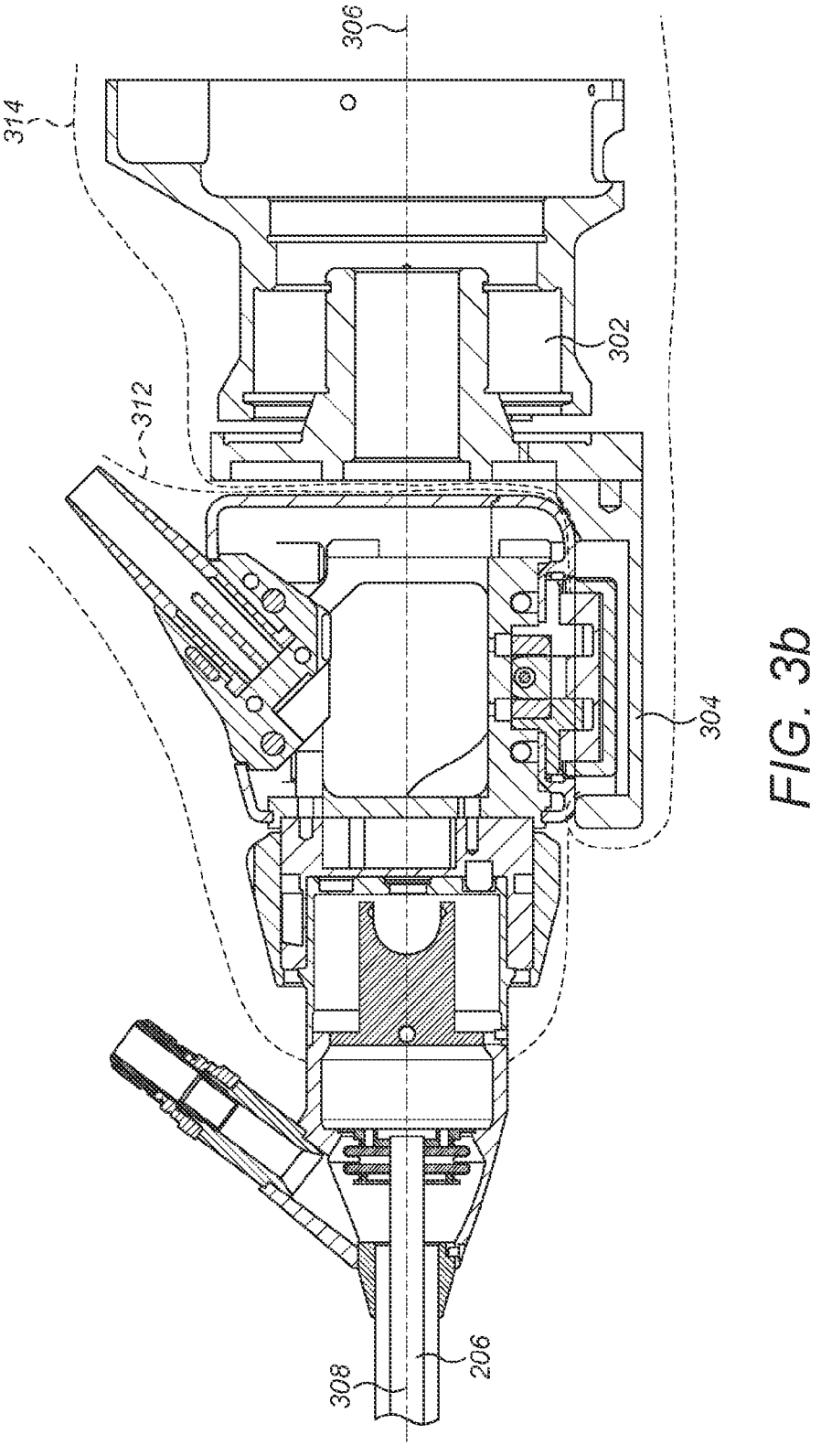

The endoscope interface 204 engages a complementary interface of the robot arm. FIG. 3*a* illustrates an endoscope being brought into engagement with the robot arm, and FIG. 3*b* illustrates the endoscope and robot arm in an engaged configuration. Suitably, the endoscope does not have an articulated distal end. Thus, there is no transfer of drive (for example cable drive) from the robot arm to the endoscope through the robot arm and endoscope interfaces. The robot arm only acts to support the endoscope. Since the endoscope is a rigid extension of the distal end of the robot arm, the orientation of the distal end of the endoscope matches that of the distal end of the robot arm. The distance that the endoscope is inserted into the patient through the port is controlled by the joint configuration of the robot arm. In other words, the distance that the endoscope is inserted into the patient through the port is controlled by the distance between the distal end of the robot arm and the port.

The endoscope is attachable to and detachable from the robot arm via the robot arm and endoscope interfaces. Suitably, the endoscope is operable independently of the robot arm in its detached state. In other words, the endoscope can be operated manually by a member of the operating room staff when detached from the robot arm.

With reference to FIGS. 3*a* and 3*b*, the distal end of the robot arm 302 terminates in the robot arm interface 304. The distal link of the robot arm 302 has a longitudinal axis 306. The endoscope shaft 206 has a longitudinal axis 308. As can be seen in FIG. 3*b*, when the endoscope is docked on the robot arm, the longitudinal axis of the endoscope shaft 308 is aligned with the longitudinal axis of the robot arm 306. By aligning the longitudinal axes of the endoscope and robot arm, the additional swept volume resulting from the size of the proximal end of the endoscope exceeding the size of the distal end of the robot arm is minimised. If the endoscope is mounted off-axis with the distal end of the robot arm, then for the same size of proximal end of the endoscope, the swept volume of the endoscope is larger. Thus, by aligning the longitudinal axes of the endoscope and distal end of the robot arm, the overall working space of the surgical robot is reduced. Thus other surgical robots can be located closer to the surgical robot supporting the endoscope whilst avoiding clashes.

Figure 4:
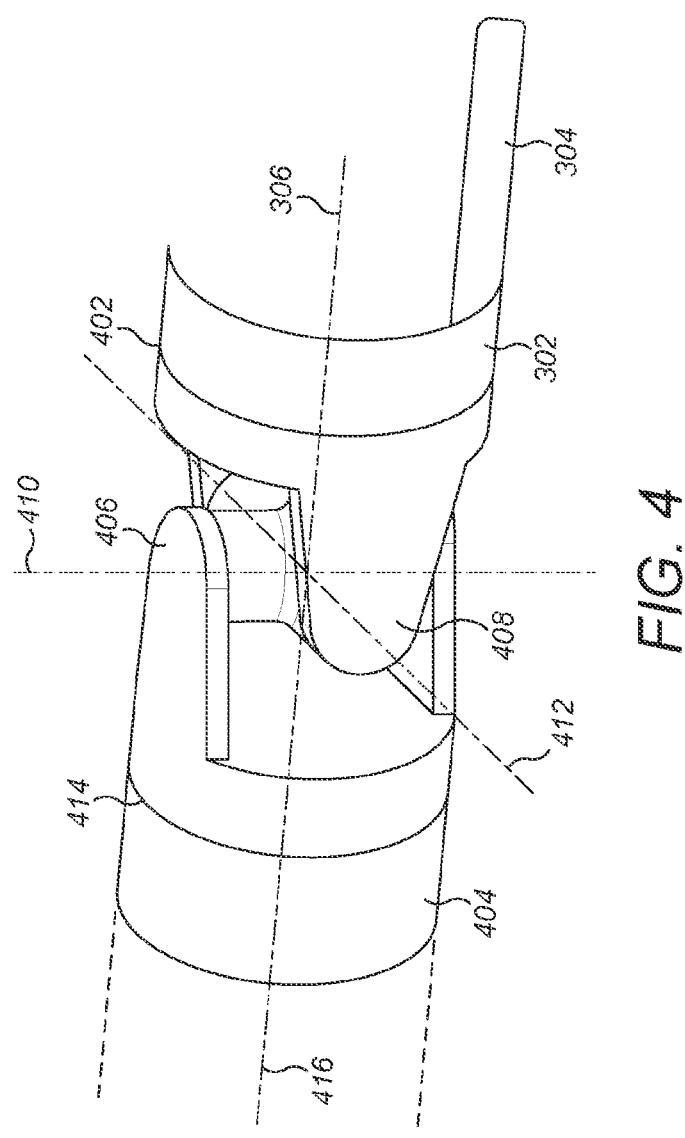
FIG. 4 illustrates the distal end of a robot arm.

FIG. 4 illustrates an exemplary distal end of the robot arm. The final joint of the robot arm of FIG. 4 is a roll joint 402. The roll joint 402 enables the distal link of the robot arm 302 to rotate about the roll joint axis 306 relative to the next link of the robot arm 404. The axis of the roll joint 306 is aligned with the longitudinal axis of the distal end of the robot arm. In FIG. 4, the distal link of the robot arm 302 is connected to the next robot arm link 404 by a compound joint. This compound joint comprises the roll joint 402. The compound joint also comprises a pitch joint 406 and a yaw joint 408. The pitch joint axis 410 intersects the yaw joint axis 412. The roll joint axis 306, the pitch joint axis 410 and the yaw joint axis 412 all intersect at the same point. Thus, when the endoscope is docked to the robot arm, the longitudinal axis of the endoscope 308 is aligned with the roll joint axis 306 and intersects the pitch joint axis 410 and the yaw joint axis 412. The compound joint may further comprise a further roll joint 313 whose roll joint axis 416 is aligned with the longitudinal axis of the penultimate link of the robot arm 404.

Referring back to FIGS. 3*a* and 3*b*, the endoscope interface and robot arm interface are located (on the endoscope and robot arm respectively) and shaped such that in order to engage each other, the endoscope and robot arm are brought together perpendicular to the longitudinal axis of the endoscope 308 and also perpendicular to the longitudinal axis of the robot arm 306. In the example of FIGS. 3*a* and 3*b*, the robot arm interface 304 extends primarily in directions parallel to the longitudinal axis 306 of the distal link of the robot arm and transverse to the longitudinal axis 306 of the distal link of the robot arm. Similarly, the endoscope interface 204 extends primarily in directions parallel to the longitudinal axis 308 of the surgical endoscope and transverse to the longitudinal axis 308 of the surgical endoscope. Both interfaces are substantially planar.

The robot arm interface 304 also comprises a rim 310 transverse to the longitudinal axis of the robot arm 306. The rim limits the length of the robot arm interface 304 which can receive and retain the endoscope interface in the direction of the longitudinal axis 306 of the distal link of the robot arm. This length is limited to be the length of the endoscope interface in the direction of the longitudinal axis 308 of the endoscope. Thus, the rim acts to constrain the robot arm interface such that it can only receive and engage the endoscope interface when the endoscope interface is brought into engagement with the robot arm interface in a direction perpendicular to the longitudinal axis of the distal link of the robot arm. In other words, the endoscope interface cannot be brought into engagement with the robot arm interface with a component of motion in the direction of the longitudinal axis of the distal end of the robot arm 306.

Not moving the endoscope in the direction of the longitudinal axis of the endoscope 308 when detaching the endoscope increases the safety of the detachment action. This is because if the endoscope was detached from the robot arm when it was still in the patient, this action would not cause the endoscope to be pushed further into the surgical site where such a movement could cause significant damage.

Suitably, the endoscope is attachable to and detachable from the robot arm by a person one-handed. A mechanism is used to engage and lock the endoscope and robot arm together. The mechanism is operated mechanically by a person. The mechanism is all contained within one of the endoscope interface and robot arm interface. By locating all the moving parts of the endoscope interface and robot arm interface in one of the endoscope interface and robot arm interface, the endoscope can be attached to and detached from the robot arm one-handed.

Figure 5:
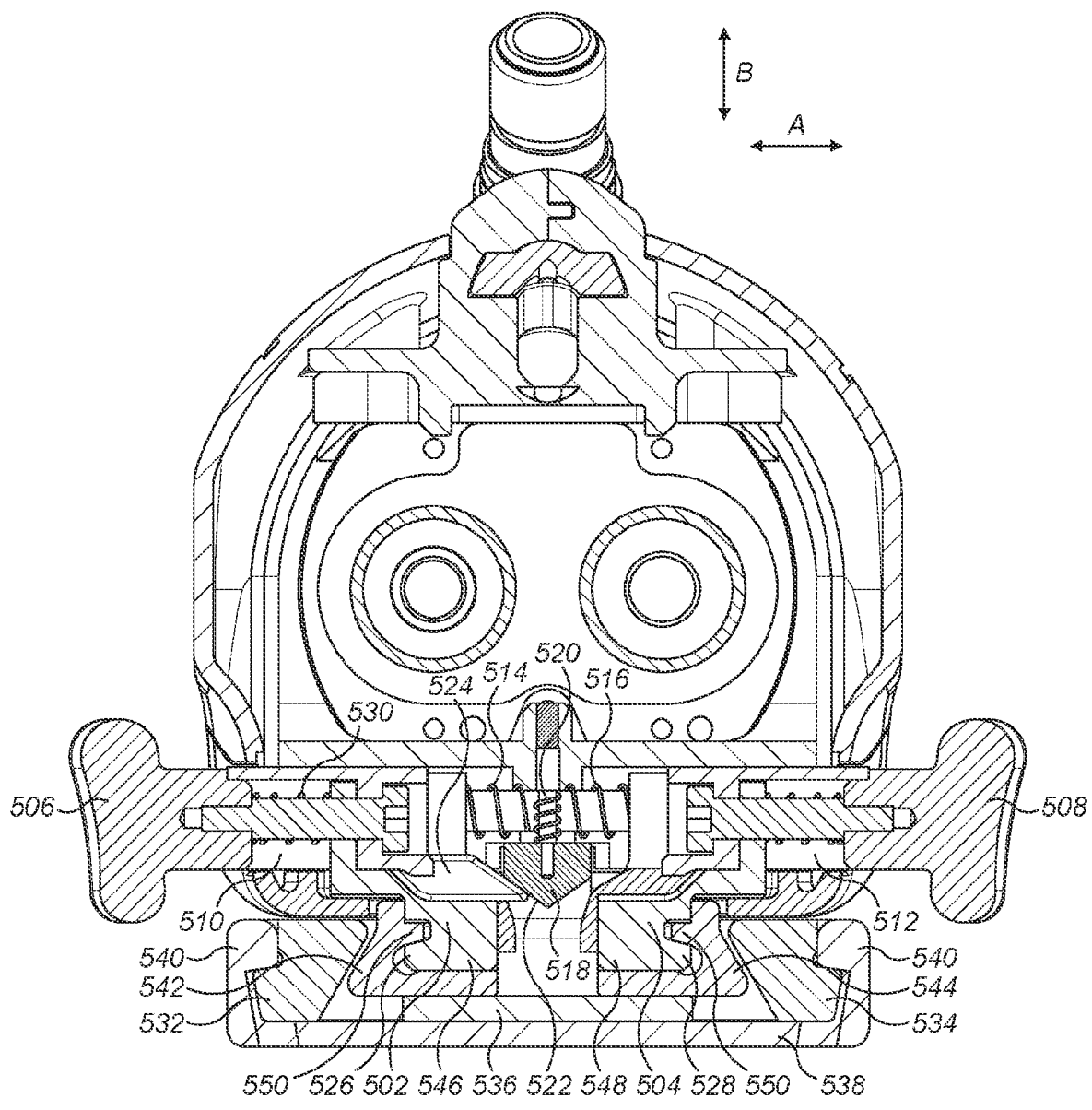
FIGS. 5, 6 and 7 illustrate a cross-section through an endoscope and robot arm in various stages of their engagement.
Figure 6:
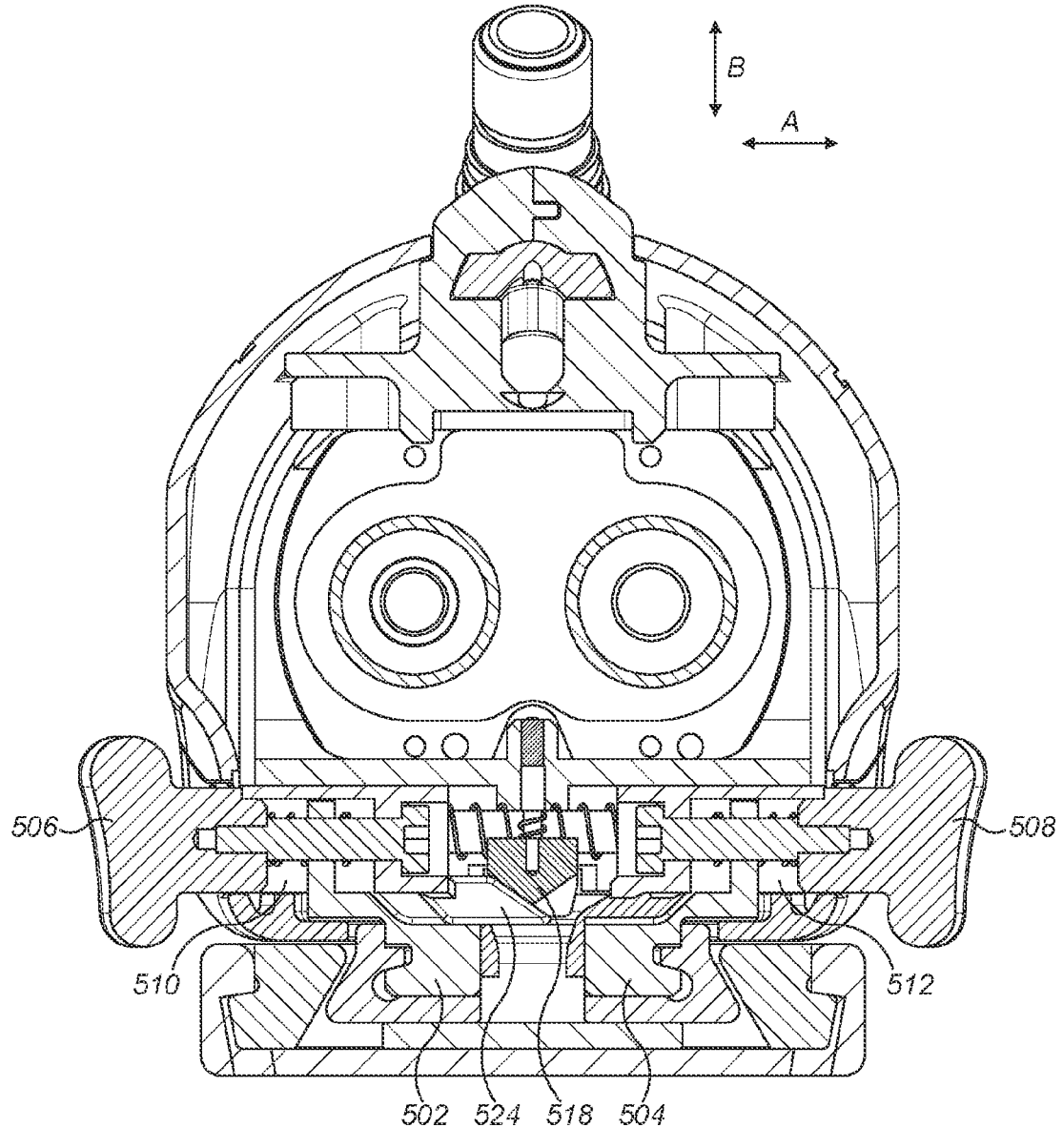
Figure 7:
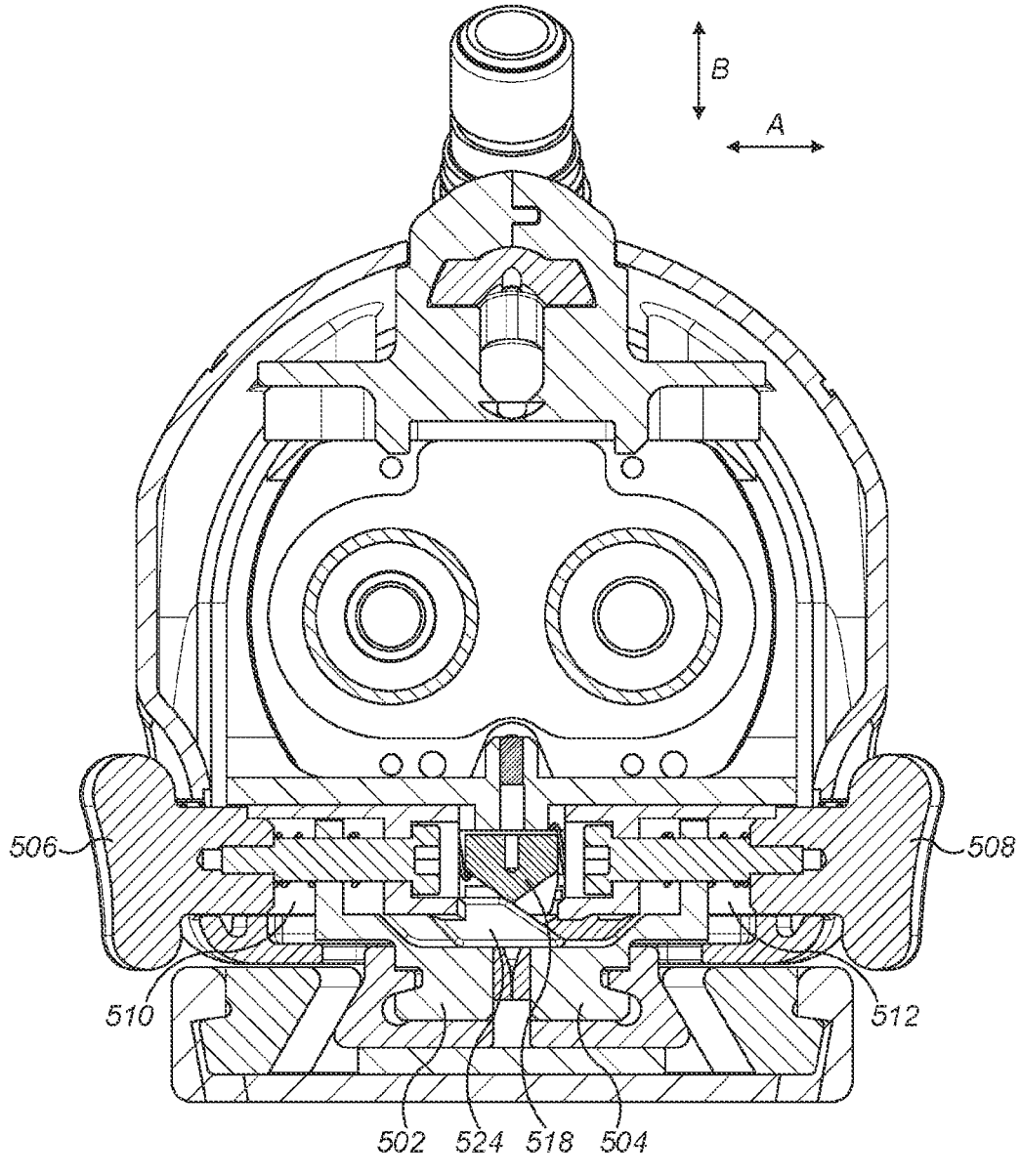

FIGS. 5, 6 and 7 illustrate a cross-section through an exemplary endoscope and robot arm in various stages of their engagement. The cross-section is in a plane perpendicular to the longitudinal axes of the robot arm 306 and endoscope 308. In FIG. 5, the endoscope and robot arm are locked in engagement. In FIGS. 6 and 7, the endoscope and robot arm are partially engaged. In the example shown in FIGS. 5 to 7, the mechanism used to engage and lock the endoscope and robot arm together is wholly contained within the endoscope interface. The robot arm interface comprises static components only. In an alternative example, the mechanism used to engage and lock the endoscope and robot arm together may be wholly contained within the robot arm interface. In this case, the endoscope interface may comprise static components only.

Referring to FIG. 5, the endoscope interface comprises an endoscope wedge mechanism. The endoscope wedge mechanism is actuated by a user to engage and disengage the endoscope from the robot arm. The mechanism is moveable between an unlocked position and a locked position. The endoscope wedge mechanism comprises endoscope wedge elements 502, 504 which are movable. The wedge elements protrude from the profile of the endoscope. It is the wedge elements which are retained in the robot arm interface when the endoscope and robot arm are engaged. The wedge elements displace when the user actuates the wedge mechanism. Collective displacement of the endoscope wedge elements actuates the endoscope wedge mechanism between its unlocked position and its locked position.

FIG. 5 illustrates two endoscope wedge elements 502, 504. The endoscope wedge elements are separated in a direction A perpendicular to the longitudinal axis 308 of the endoscope. By comparing the locked position of FIG. 5 to the unlocked position of FIG. 7, it can be seen that the endoscope wedge elements are separated by a greater distance in the direction A in the locked position than in the unlocked position. The endoscope wedge elements 502, 504 are displaceable in the direction A. The endoscope wedge elements 502, 504 displace towards each other to move the endoscope wedge mechanism towards its unlocked position. The endoscope wedge elements 502, 504 displace away from each other to move the endoscope wedge mechanism towards its locked position.

Each endoscope wedge element is connected to an arm 510, 512 which terminates in a user contact 506, 508 at the exterior of the endoscope's proximal end. The arms may be aligned as shown in FIGS. 5-7. The user contacts may be exposed external to the profile of the endoscope when the endoscope wedge mechanism is in its locked state. The user contacts may be exposed on opposing sides of the exterior of the endoscope as shown in FIGS. 5-7. The user contacts are depressible by a user. Each arm is displaceable in the direction A. A user depresses the user contact 506, 508 in the direction A thereby causing the arm and hence the endoscope wedge element to displace in the direction A. The two user contacts 506, 508 and hence the two arms 510, 512 of the endoscope wedge elements 502, 504 displace towards each other to move the endoscope wedge mechanism towards its unlocked position. The two user contacts 506, 508 and hence the two arms 510, 512 of the endoscope wedge elements 502, 504 displace away from each other to move the endoscope wedge mechanism towards its locked position.

The endoscope wedge elements may be biased towards their configuration in the locked position of the endoscope wedge mechanism. In the example of FIGS. 5-7, the endoscope wedge elements 502, 504 are spring-biased towards their configuration in the locked position of the endoscope wedge mechanism. Spring 514 resists displacement of the arm 510 and hence the endoscope wedge element 502 in the direction A towards the other endoscope wedge element 504. Spring 514 provides a spring force which opposes the force applied by the user to the user contact 506. In the example of FIGS. 5-7, spring 514 is within arm 510 and wound so as to compress and expand in the direction A. When the user applies a user force to the user contact 506 which exceeds the opposing force of the spring 514, the endoscope wedge mechanism moves towards the unlocked position. When the user releases the user contact 506, the spring force is greater than the user force, thus the endoscope wedge mechanism moves back to the locked position. Spring 516 resists displacement of the arm 512 and hence the endoscope wedge element 504 in the direction A towards the other endoscope wedge element 504. Spring 516 provides a spring force which opposes the force applied by the user to the user contact 508. In the example of FIGS. 5-7, spring 516 is within arm 512 and wound so as to compress and expand in the direction A. Spring 516 may be the same spring as spring 514. When the user applies a user force to the user contact 508 which exceeds the opposing force of the spring 516, the endoscope wedge mechanism moves towards the unlocked position. When the user releases the user contact 508, the spring force is greater than the user force, thus the endoscope wedge mechanism moves back to the locked position. Thus, by applying opposing user forces to the user contacts 506, 508 which exceed the forces of springs 514, 516, the user moves the endoscope wedge mechanism away from the locked position of FIG. 5 towards the unlocked position of FIG. 7.

The endoscope wedge mechanism may further comprise a lock which constrains the endoscope wedge elements to their configuration in the locked position of the endoscope wedge mechanism. The lock does not constrain the endoscope wedge elements in the unlocked position of the endoscope wedge mechanism. In the example of FIGS. 5-7, the lock comprises a plunger 518 which is moveable in a direction B transverse to the direction A. In the locked position shown in FIG. 5, the plunger 518 wedges the endoscope wedge elements 502, 504 apart. In the unlocked positions shown in FIGS. 6 and 7, the plunger does not impede the position of the endoscope wedge elements 502, 504 in the direction A. The plunger is biased towards its configuration in the locked position. In the example of FIG. 5, the plunger is spring-biased towards the locked position by spring 520. Spring 520 provides a spring force in the direction B which pushes the plunger in between the endoscope wedge elements. Spring 520 is wound about the longitudinal axis of plunger 518 so as to compress and expand in the direction B.

The endoscope wedge element 502 of FIG. 5 comprises two parts which are moveable relative to each other: a mating wedge 526, and a projection 524. The mating wedge 526 mates with a complementary robot arm wedge element of the robot arm interface. The plunger 518 comprises a surface feature which engages the projection 524. In FIG. 5, this surface feature is an angled lead-in 522. The projection 524 has a complementary shape to the angled lead-in 522.

The projection 524 is biased towards its configuration in the locked position of the endoscope wedge mechanism. In the example of FIGS. 5-7, the projection 524 is spring-biased towards its configuration in the locked position of the endoscope wedge mechanism. Spring 530 resists displacement of the arm 510 and hence the projection 524 in the direction A towards the plunger 518. Spring 530 provides a spring force which opposes the force applied by the user to the user contact 506. Spring 530 is within arm 510 and wound so as to compress and expand in the direction A. When the user applies a user force to the user contact 506 which exceeds the opposing force of the spring 530, the projection 524 moves in the direction A towards the plunger 518. By virtue of the angled shapes of the projection 524 and lead-in 522, once the projection contacts the plunger 518, as the projection 524 moves further towards the plunger, the plunger moves in the direction B away from between the mating wedges 526, 528. The force of the projection 524 on the plunger 518 overcomes the spring bias of spring 520, thereby causing the plunger 518 to displace in the direction B away from between the mating wedges 526, 528. FIG. 6 illustrates the projection 524 having moved its maximum displacement towards the plunger 518. The plunger 518 is not obstructing the motion of the mating wedges 526, 528. When the user releases the user contact 506, the force of spring 530 is greater than the user force, thus the projection 518 moves in the direction A away from the plunger 518, which consequently causes the plunger to move between the mating wedges 526, 528.

Although only one projection 524 and one plunger 518 are illustrated in FIGS. 5-7, two or more projections may engage one or more plungers. The projections may be connected to one or both arms.

In the example of FIGS. 5-7, the projection 524 and mating wedge 526 are both subject to biasing forces in the same direction, from springs 530 and 514 respectively. Displacement of both the projection 524 and the mating wedge 526 are actuated by application of force to the same user contact 506. The biasing force of the projection is selected to be lower than the biasing force of the mating wedge, for example by the projection being more lightly sprung than the mating wedge. Thus, when the user applies force to the user contact, the biasing force of the projection is overcome before the biasing force of the mating wedge. Thus, when the user applies force to the user contact in the locked position of the endoscope wedge mechanism, the projection 524 moves towards the plunger 518 in the direction A before the mating wedge 526 moves towards the other mating wedge 528 in the direction A. Thus, on application of force by the user to the user contact, the endoscope wedge mechanism moves from the locked configuration of FIG. 5 in which the plunger 518 wedges the mating wedges 526, 528 apart to the unlocked configuration of FIG. 6 in which the plunger 518 has moved out from between the mating wedges 526, 528. On further application of force by the user to the user contact, the endoscope wedge mechanism moves from the unlocked configuration of FIG. 6 to the disengageable configuration of FIG. 7 in which the endoscope interface can be removed from the robot arm interface.

Although above two endoscope wedge elements 502, 504 have been described, further endoscope wedge elements may be utilised. These further endoscope wedge elements may be actuated by the same user contacts shown in FIGS. 5-7, or by further user contacts.

The robot arm interface of FIGS. 5 to 7 will now be described. The robot arm interface comprises robot arm interface elements for engaging the endoscope interface elements. More specifically, the robot arm interface comprises robot arm wedge elements 532, 534 for retaining the endoscope wedge elements 502, 504. Both the endoscope wedge elements 502, 504 and the robot arm wedge elements 532, 534 have a surface at an angle to the direction in which the endoscope interface is brought into engagement with the robot arm interface. The angled surface of the endoscope wedge element 502 contacts the angled surface of the robot arm wedge element 532. The angled surface of the endoscope wedge element 504 contacts the angled surface of the robot arm wedge element 534. The contact surfaces are angled such that when the endoscope interface and the robot arm interface are engaged, the robot arm wedge elements 532, 534 constrain the endoscope wedge elements in the direction in which the endoscope interface is brought into engagement with the robot arm interface. In other words, in the locked position shown in FIG. 5, the angled surfaces of the robot arm wedge elements 532, 534 prevent the endoscope interface from being lifted away from the robot arm interface in the direction B. The endoscope interface is also prevented from being lifted away from the robot arm interface in any other direction. Hence a lateral force on the end of the endoscope does not cause the endoscope interface to become detached from the robot arm interface. Each robot arm wedge element has a complementary shape to the endoscope wedge element that it retains.

Figure 8A:
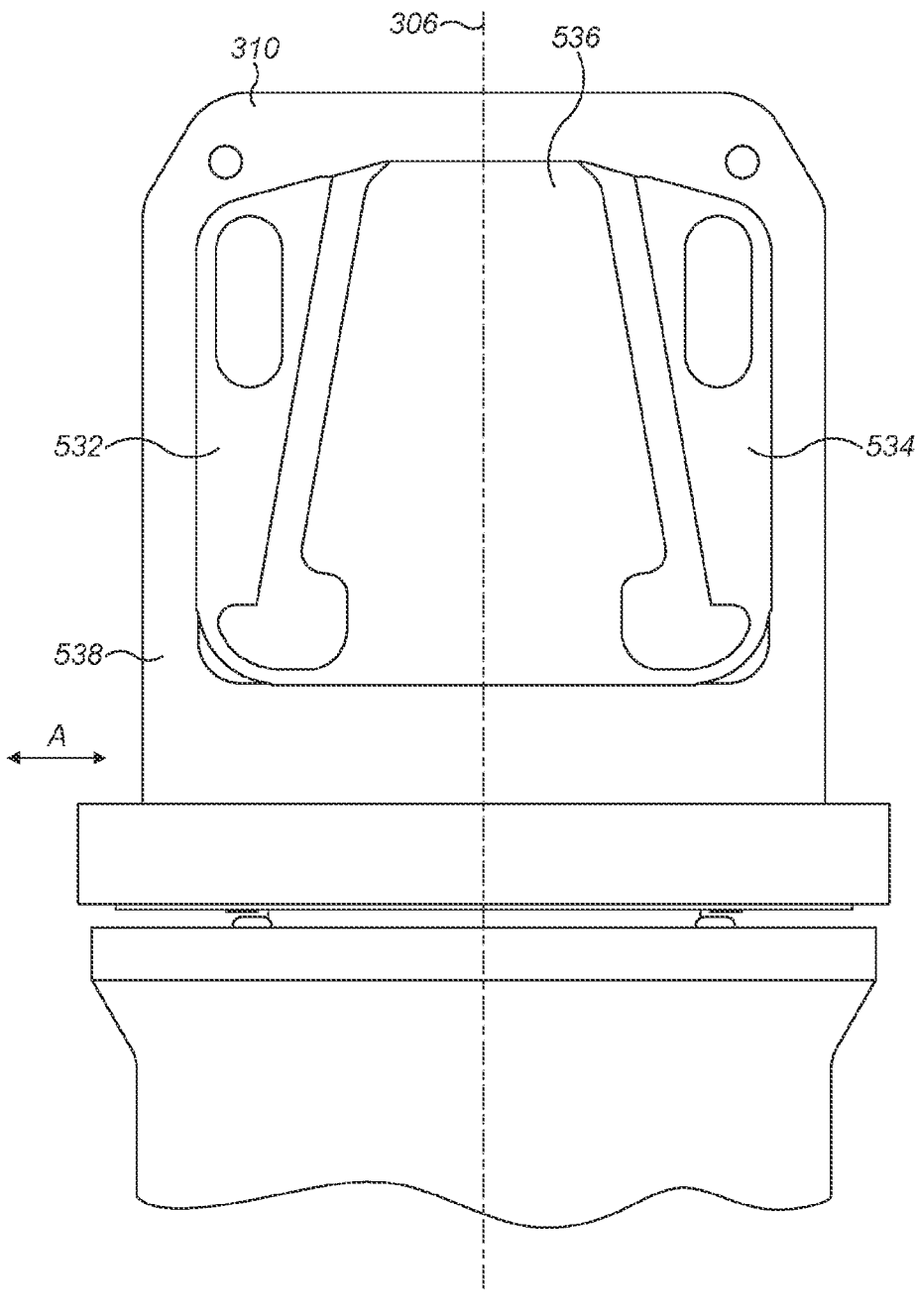
FIGS. 8*a* and 8*b* illustrate cross sections of the endoscope interface and robot arm interface which are transverse to the cross sections of FIGS. 5 to 7.
Figure 8B:
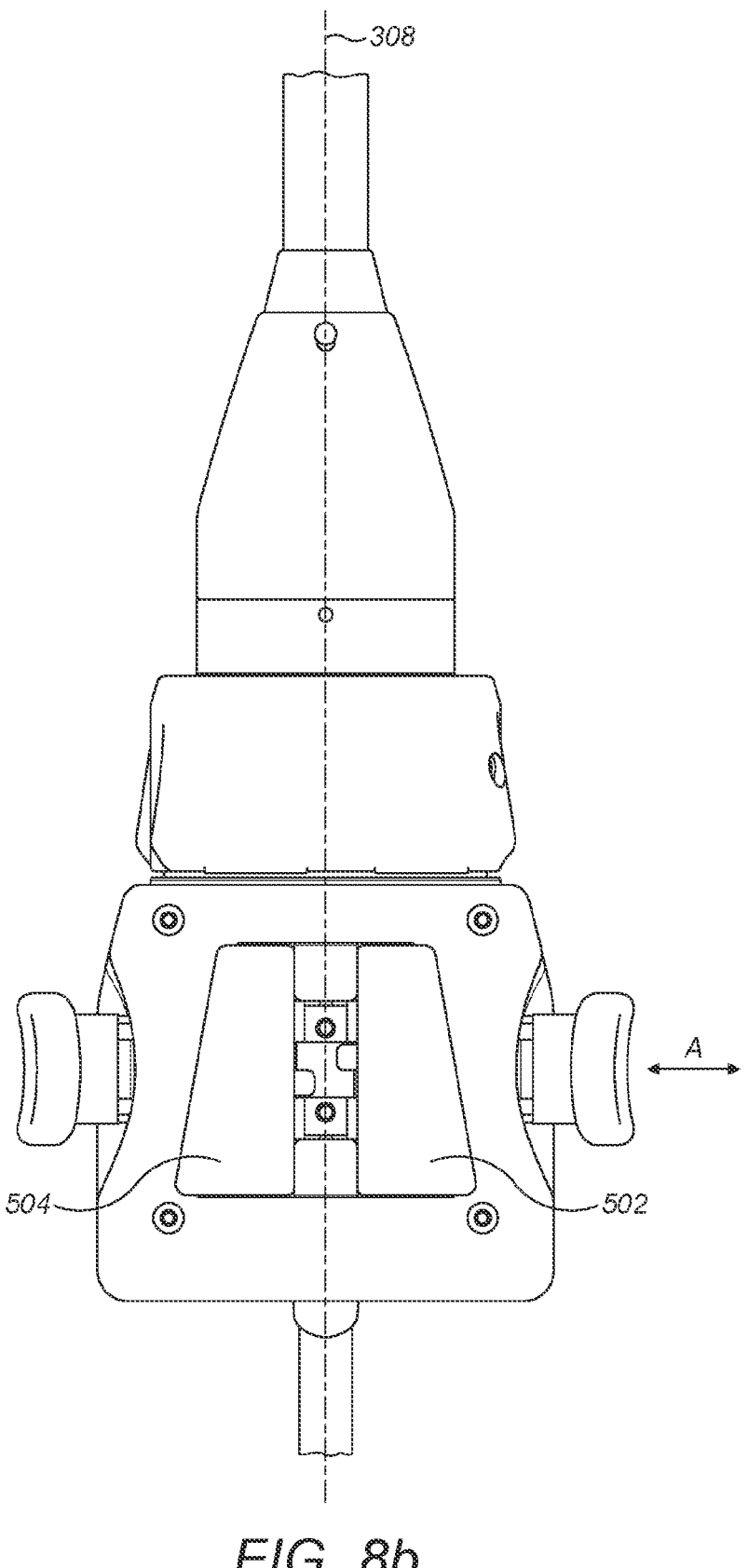

The separation of the robot arm wedge elements 532, 534 may vary over the length of the robot arm interface. FIGS. 8a and 8b illustrate cross sections of the endoscope interface and robot arm interface which are transverse to the cross sections of FIGS. 5 to 7 and parallel to the longitudinal axes 308 and 306 of the endoscope shaft and distal link of the robot arm. FIG. 8a illustrates the robot arm interface, and FIG. 8b illustrates the endoscope interface. The separation of the robot arm wedge elements 532, 534 can be seen to vary in the direction of the longitudinal axis of the terminal link of the robot arm 306. The separation of the robot arm wedge elements 532, 534 decreases the more distal they are from the distal link of the robot arm. The width of the endoscope wedge elements 502, 504 in the direction A can be seen to vary over the length of the endoscope interface so as to match the separation of the robot arm wedge elements over the length of the robot arm interface. Thus, the endoscope interface engages the robot arm interface in one position only.

In order to ensure a sterile environment, components which are used in the operating room are either pre-sterilised or covered by a sterile drape. Suitably, both the robot arm and the endoscope are draped in order to maintain the sterile barrier with the patient. The robot arm and endoscope may be individually draped. By separately draping the robot arm and the endoscope, the endoscope can be removed from the robot arm and used independently of the robot arm whilst still maintaining the sterile barrier to the patient. FIGS. 3a and 3b illustrate an endoscope drape 312 which covers the endoscope (or the portion of the endoscope which is non-sterile) and a robot arm drape 314 which covers the robot arm.

The sterile barrier continues across the robot arm interface and the endoscope interface. In one arrangement, one or more components of the robot arm interface may be integral to the robot arm drape. For example, one or more components of the robot arm interface may be bonded to the robot arm drape. Similarly, one or more components of the endoscope interface may be integral to the endoscope drape. For example, one or more components of the endoscope interface may be bonded to the endoscope drape. Thus, the robot arm interface comprises components which are part of the robot arm and components which are part of the robot arm drape. Similarly, the endoscope interface comprises components which are part of the endoscope and components which are part of the endoscope drape. When the endoscope interface engages the robot arm interface, contact is between the endoscope drape and the robot arm drape.

In this arrangement, with reference to FIG. 5, the robot arm drape comprises the robot arm wedge elements 532, 534. The robot arm drape also comprises reinforcing element 536. The robot arm comprises the body 538 of the robot arm interface. The body 538 retains the robot arm drape elements 532, 534 and 536. These robot arm drape elements are detachable from the body. The body 538 comprises a lip 540 which retains each of the robot arm wedge elements 532, 534 and the reinforcing element 536. The body 538 also comprises the rim 310.

The endoscope mating wedges 526, 528 each comprise an endoscope drape wedge element 542, 544 which is part of the endoscope drape, and an endoscope assembly wedge element 546, 548 which is part of the endoscope. The endoscope drape wedge elements are detachable from the endoscope assembly wedge elements. The endoscope drape wedge elements 542, 544 are retained by the endoscope assembly wedge elements 546, 548. The contact surfaces of the endoscope drape wedge elements 542, 544 are complementarily shaped to the endoscope assembly wedge elements 546, 548. The endoscope assembly wedge elements 546, 548 comprise surface features such as nibs 550 which retain complimentary shaped surface features of the endoscope drape wedge elements 542, 544. These surface features act to fasten the endoscope drape wedge elements to the endoscope assembly wedge elements, and hence resist forces acting to detach the endoscope from the endoscope drape.

In an alternative arrangement, the portion of the robot arm drape across the robot arm interface may not comprise any of the components of the robot arm interface. For example, this portion of the robot arm drape may be composed of fabric only with no rigid components. This fabric may be the same as the fabric of the remainder of the robot arm drape. Alternatively, the fabric across the robot arm interface may be reinforced relative to the fabric of the remainder of the robot arm drape. The portion of the endoscope drape across the endoscope interface may not comprise any of the components of the endoscope interface. For example, this portion of the endoscope drape may be composed of fabric only with no rigid components. This fabric may be the same as the fabric of the remainder of the endoscope drape. Alternatively, the fabric across the endoscope interface may be reinforced relative to the fabric of the remainder of the endoscope drape. In these arrangements, any one or more of the robot arm wedge elements 532, 534 and the reinforcing element 536 may be integral with the body 538 of the robot arm interface. These components are not detachable from the robot arm interface, and hence not detachable from the robot arm in use. Similarly, each endoscope mating wedge may be integrally formed. In other words, endoscope mating wedge 526 does not comprise detachable components 542 and 546; and endoscope mating wedge 528 does not comprise detachable components 544 and 548. These components are not detachable from the endoscope interface, and hence not detachable from the endoscope in use.

A replica endoscope interface may be utilised during a process of characterising the environment of the surgical robot. The replica endoscope interface comprises an endoscope wedge mechanism as described herein. Suitably, the replica endoscope interface does not comprise any other features of an endoscope. The replica endoscope interface may be located at a known location in the operating room, such as at a known location on the patient table. During setup of the endoscope robot arm prior to an operation, the robot arm interface is brought to the replica endoscope interface and the two are engaged using the procedure described herein. The control system of the robot arm uses the known configuration of the joints of the robot arm (from joint configuration signals received from position sensors on the robot arm), the known position and orientation of the replica endoscope interface, and the known position and orientation of the robot arm interface when in engagement with the replica endoscope interface to determine the position of the robot arm in the operating room. The control system may also use torque measurements from torque sensors on the robot arm to determine the direction of gravity acting on the robot arm, and hence determine the orientation of the robot arm.

The endoscope and robot arm could be used for non-surgical purposes. For example, the endoscope could be used in an industrial robot manufacturing or machining procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

What is claimed is:

1. A surgical robot for manipulating a surgical endoscope, the surgical robot comprising:
    a robot base connected to a distal robot arm link via a series of intermediate articulated robot arm links;
    a robot arm interface attached to the distal robot arm link; and
    a surgical endoscope comprising:
        a shaft having a distal end for insertion into a patient and a proximal end; and
        an endoscope interface attached to the proximal end of the shaft;
        wherein the robot arm interface is configured to receive and engage the endoscope interface such that the longitudinal axis of the distal robot arm link is aligned with the longitudinal axis of the surgical endoscope, wherein the robot arm interface is shaped so as to only receive and engage the endoscope interface when the endoscope interface and robot arm interface are brought into engagement in a direction perpendicular to the longitudinal axis of the distal robot arm link, and wherein the robot arm interface is shaped so as to only disengage the endoscope interface when the endoscope interface and robot arm interface are moved out of engagement in a direction perpendicular to the longitudinal axis of the distal robot arm link;

wherein the robot arm interface primarily extends parallel to the longitudinal axis of the distal robot arm link and transverse to the longitudinal axis of the distal robot arm link;

wherein the robot arm interface comprises a rim transverse to the longitudinal axis of the distal robot arm link, the rim acting to constrain the robot arm interface to only being able to receive and engage the endoscope interface when the endoscope interface is brought into engagement with the robot arm interface in a direction perpendicular to the longitudinal axis of the distal robot arm link; and wherein the rim limits the length of the robot arm interface which can receive and retain the endoscope interface in the direction of the longitudinal axis of the distal robot arm link to be the length of the endoscope interface in the direction of the longitudinal axis of the endoscope.

2. A surgical robot as claimed in claim 1, wherein the distal robot arm link is attached to a second robot arm link by a roll joint, the longitudinal axis of the surgical endoscope being aligned with the roll axis of the roll joint.

3. A surgical robot as claimed in claim 1, wherein the distal robot arm link is attached to the second robot arm link by a compound joint, the compound joint permitting the distal robot arm link to rotate about a roll axis, a pitch axis, and a yaw axis relative to the second robot arm link, the longitudinal axis of the surgical endoscope intersecting the pitch axis and the yaw axis.

4. A surgical robot as claimed in claim 1, wherein the robot arm interface is shaped so as to only receive and engage the endoscope interface when the endoscope interface and robot arm interface are brought into engagement in a direction perpendicular to the longitudinal axis of the surgical endoscope.

5. A surgical robot as claimed in claim 1, wherein the surgical endoscope is operable when detached from the distal robot arm link.

6. A surgical robot as claimed in claim 1, the endoscope interface comprising:

an endoscope wedge mechanism moveable between an unlocked position and a locked position, the endoscope wedge mechanism comprising:

endoscope wedge elements which are displaceable such that collective displacement of the endoscope wedge elements actuates the endoscope wedge mechanism between the unlocked position and the locked position.

7. A surgical robot as claimed in claim 6, wherein the endoscope interface is configured to be received in the robot arm interface such that the endoscope wedge elements are retained by complementary robot arm wedge elements when the endoscope interface and robot arm interface are engaged.

8. A surgical robot as claimed in claim 6, wherein the endoscope interface primarily extends parallel to the longitudinal axis of the surgical endoscope and transverse to the longitudinal axis of the surgical endoscope.

9. A surgical robot as claimed in claim 6, wherein each endoscope wedge element is displaceable transverse to the longitudinal axis of the surgical endoscope.

10. A surgical robot as claimed in claim 6, wherein the endoscope wedge elements are biased towards their configuration in the locked position of the endoscope wedge mechanism.

11. A surgical robot as claimed in claim 10, wherein the endoscope wedge elements are spring-biased towards their configuration in the locked position of the endoscope wedge mechanism.

12. A surgical robot as claimed in claim 6, comprising two endoscope wedge elements configured to be separated by a greater distance in the locked position of the endoscope wedge mechanism than in the unlocked position of the endoscope wedge mechanism.

13. A surgical robot as claimed in claim 6, the endoscope interface comprising an endoscope assembly and an endoscope drape, the endoscope drape being detachable from the endoscope assembly.

14. A surgical robot as claimed in claim 1, the robot arm interface further comprising robot arm interface elements for engaging endoscope interface elements of the endoscope interface, all the robot arm interface elements being static in the robot arm interface.

15. A surgical robot as claimed in claim 1, wherein the robot arm interface is configured to receive and engage the endoscope interface such that the longitudinal axis of the distal robot arm link is collinear with the longitudinal axis of the surgical endoscope.

16. A surgical robot as claimed in claim 1, wherein the rim acts to constrain the robot arm interface to only be able to disengage the endoscope interface when the endoscope interface is moved out of engagement with the robot arm interface in a direction perpendicular to the longitudinal axis of the distal robot arm link.

* * * * *